(12) United States Patent
Koike

(10) Patent No.: US 11,653,970 B2
(45) Date of Patent: May 23, 2023

(54) PLASMA GUIDE WIRE

(71) Applicant: ASAHI INTECC CO., LTD., Seto (JP)

(72) Inventor: Tadahiro Koike, Seto (JP)

(73) Assignee: ASAHI INTECC CO., LTD., Seto (JP)

( * ) Notice: Subject to any disclaimer, the term of this patent is extended or adjusted under 35 U.S.C. 154(b) by 767 days.

(21) Appl. No.: 16/677,758

(22) Filed: Nov. 8, 2019

(65) Prior Publication Data
US 2020/0069361 A1 Mar. 5, 2020

Related U.S. Application Data

(63) Continuation of application No. PCT/JP2017/023928, filed on Jun. 29, 2017.

(51) Int. Cl.
| | |
|---|---|
| A61B 18/14 | (2006.01) |
| A61B 17/22 | (2006.01) |
| A61B 18/04 | (2006.01) |
| A61M 25/09 | (2006.01) |

(52) U.S. Cl.
CPC .............. *A61B 18/14* (2013.01); *A61B 17/22* (2013.01); *A61B 18/042* (2013.01); *A61M 25/09* (2013.01); *A61B 2017/22042* (2013.01); *A61M 2025/09083* (2013.01); *A61M 2025/09108* (2013.01); *A61M 2025/09175* (2013.01)

(58) Field of Classification Search
CPC ....... A61B 17/22; A61B 18/14; A61B 18/042; A61M 25/09; A61M 2025/09083; A61M 2025/09108; A61M 2025/09116; A61M 2025/09133; A61M 2025/09091
See application file for complete search history.

(56) References Cited

U.S. PATENT DOCUMENTS

| | | | | |
|---|---|---|---|---|
| 5,368,035 A | * | 11/1994 | Hamm ................. | A61M 25/09 600/463 |
| 5,372,144 A | | 12/1994 | Mortier et al. | |

FOREIGN PATENT DOCUMENTS

| | | | | |
|---|---|---|---|---|
| CN | 103127599 A | * | 6/2013 | ............ A61M 25/09 |
| WO | 97/24978 A1 | | 7/1997 | |
| WO | WO-2013047616 A1 | * | 4/2013 | ............ A61M 25/09 |
| WO | 2016/134152 A1 | | 8/2016 | |
| WO | WO-2018193597 A1 | * | 10/2018 | ............ A61B 17/22 |

OTHER PUBLICATIONS

Nov. 21, 2017 International Search Report issued in International Patent Application No. PCT/JP2017/023928.

* cited by examiner

*Primary Examiner* — Catherine B Kuhlman
*Assistant Examiner* — Raymond P Dulman
(74) *Attorney, Agent, or Firm* — Oliff PLC

(57) ABSTRACT

Provided is a plasma guide wire including a core shaft, a coil, a tip, a coil-core shaft joining region, and first to third insulating resin tubes. The first insulating resin tube is disposed on the outer periphery of the coil, and extends proximally from the tip to beyond the coil-core shaft joining region. The second insulating resin tube is disposed on the outer periphery of the core shaft, is joined to the proximal end of the first insulating resin tube, and extends from the proximal end of the first insulating resin tube to the proximal side of the core shaft. The second insulating resin tube is harder than the first insulating resin tube. The third insulating resin tube is disposed on at least a portion of a region of the inner periphery of the first insulating resin tube, proximal to a location facing the proximal end of the coil.

14 Claims, 5 Drawing Sheets

PLASMA GUIDE WIRE

CROSS REFERENCE TO RELATED APPLICATION

This is a Continuation of PCT/JP2017/023928 filed Jun. 29, 2017. The disclosure of the prior application is hereby incorporated by reference herein in its entirety.

BACKGROUND

The disclosed embodiments relate to a plasma guide wire.

Conventionally, plasma guide wires are known. For example, WO 2016/134152 discloses a plasma guide wire 100 as shown in FIG. 6 including a guide wire body 120 and an insulating resin tube 130 covering the guide wire body 120. In the guide wire body 120, a coil 124 is wound around on the outer periphery of a region at the distal end side of a core shaft 122, and a tip 126 is joined to the distal end of the core shaft 122 and the distal end of the coil 124. The proximal end of the coil 124 is joined to the core shaft 122 at a coil-core shaft joining region 125. The insulating resin tube 130 includes a first insulating resin tube 131 and a second insulating resin tube 132. The first insulating resin tube 131 is disposed on the outer periphery of the coil 124, and extends proximally from the tip 126 to beyond the coil-core shaft joining region 125. The second insulating resin tube 132 is disposed on the outer periphery of the core shaft 122, is joined to the proximal end of the first insulating resin tube 131, and extends from the proximal end of the first insulating resin tube 131 to the proximal side of the core shaft 122. The plasma guide wire 100 as described above may be used to generate plasma between the distal end of the tip 126 and an electrode of a separate member facing that distal end when a high-frequency generator is connected to the proximal end of the core shaft 122. This enables plasma to perforate an occluded portion of a blood vessel.

Nonetheless, a configuration where the first insulating resin tube 131 and the second insulating resin tube 132 are composed of different materials is not mentioned in any way in WO 2016/134152. Consequently, the operativity of a portion of the guide wire body 120 where the coil 124 is wound around may be decreased if the first insulating resin tube 131 and the second insulating resin tube 132 are composed of the same relatively hard resin. On the other hand, a stiffness gap (sudden difference in stiffness) may be created at a portion of the first insulating resin tube 131 where the coil 124 is not present if the second insulating resin tube 132 is configured to be harder than the first insulating resin tube 131. This may result in the following problem: the first insulating resin tube 131, which is soft, may be bent at this portion when the plasma guide wire 100 is pushed to the distal-end direction. This, in turn, will decrease operativity.

SUMMARY

The disclosed embodiments were devised to address the problem as described above. An object of the disclosed embodiments is to improve operativity of a distal end side (that is, a portion of a core shaft where a coil is wound around and/or a portion of a first insulating resin tube where a coil is not present) of a plasma guide wire.

A plasma guide wire according to the disclosed embodiments incudes:

a core shaft, a coil wound around on an outer periphery of a region of a distal end side of the core shaft, a tip joined to a distal end of the core shaft and a distal end of the coil, a coil-core shaft joining region joining a proximal end of the coil with the core shaft, a first insulating resin tube disposed on an outer periphery of the coil and extending proximally from the tip to beyond the coil-core shat joining region, a second insulating resin tube disposed on an outer periphery of the core shaft, and joined to a proximal end of the first insulating resin tribe, and extending from the proximal end of the first insulating resin tube to a proximal side of the core shaft, the second insulating resin tube being harder than the first insulating resin tube, and a third insulating resin tube disposed on at least a portion of a region of an inner periphery of the first insulating resin tube, the region being located proximal to a position facing the proximal end of the coil.

According to the above plasma guide wire, a stiffness gap created at a portion of the relatively soft first insulating resin tube where the coil is not present can be reduced by virtue of the presence of the third insulating resin tube. This can prevent bending at this portion. Further, the third insulating resin tube is not disposed at a portion of the relatively soft first insulating resin tube where the relatively soft first insulating resin tube covers the coil. This can improve the operativity of the distal end side of the plasma guide wire, i.e., a portion of the core shaft where the coil is wound around and/or a portion of the first insulating resin tube where the coil is not present.

DETAILED DESCRIPTION THE EMBODIMENTS

Figure 1:
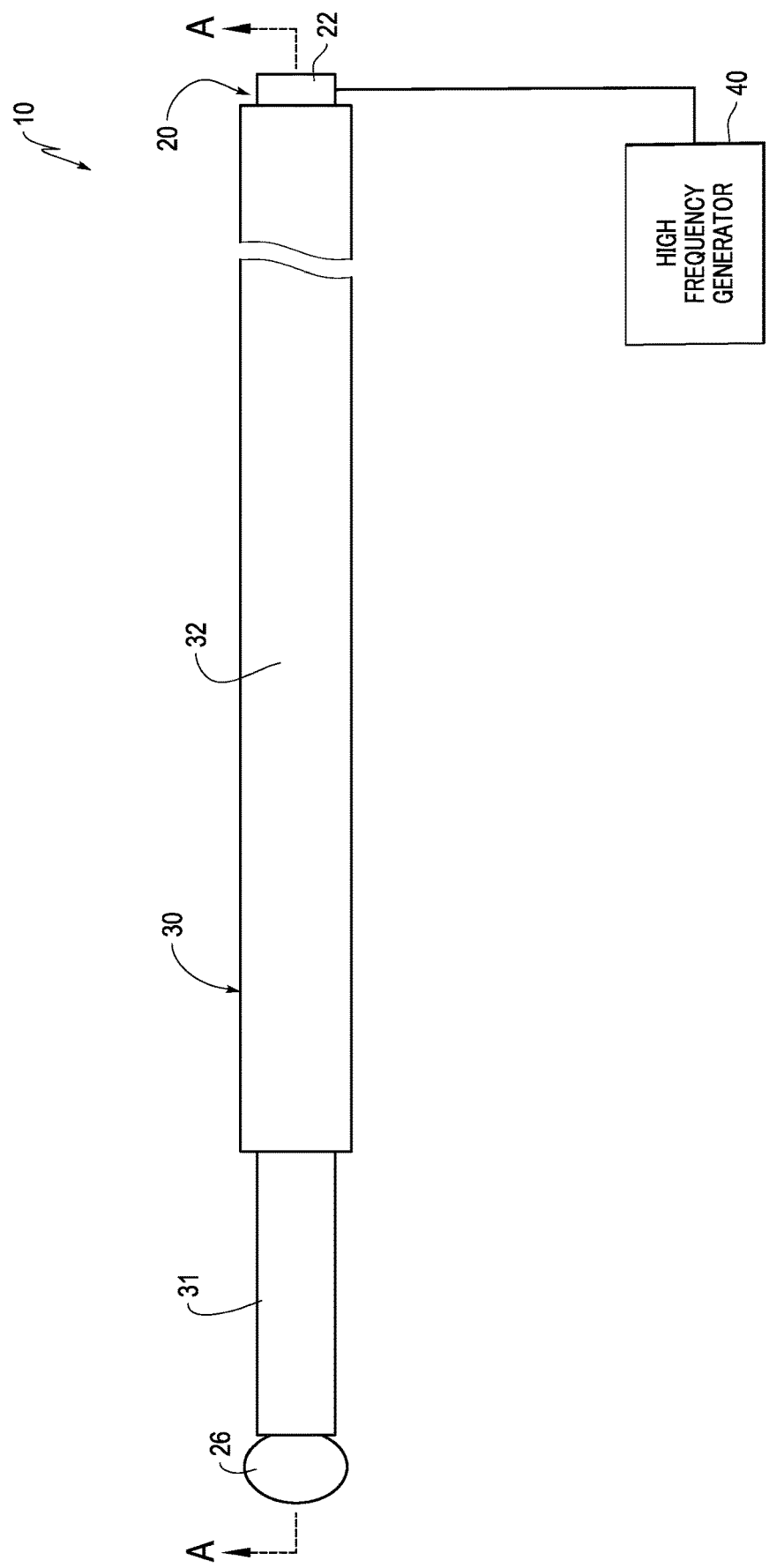
FIG. 1 shows a front elevational view of a plasma guide wire 10 according to the disclosed embodiments.
Figure 2:
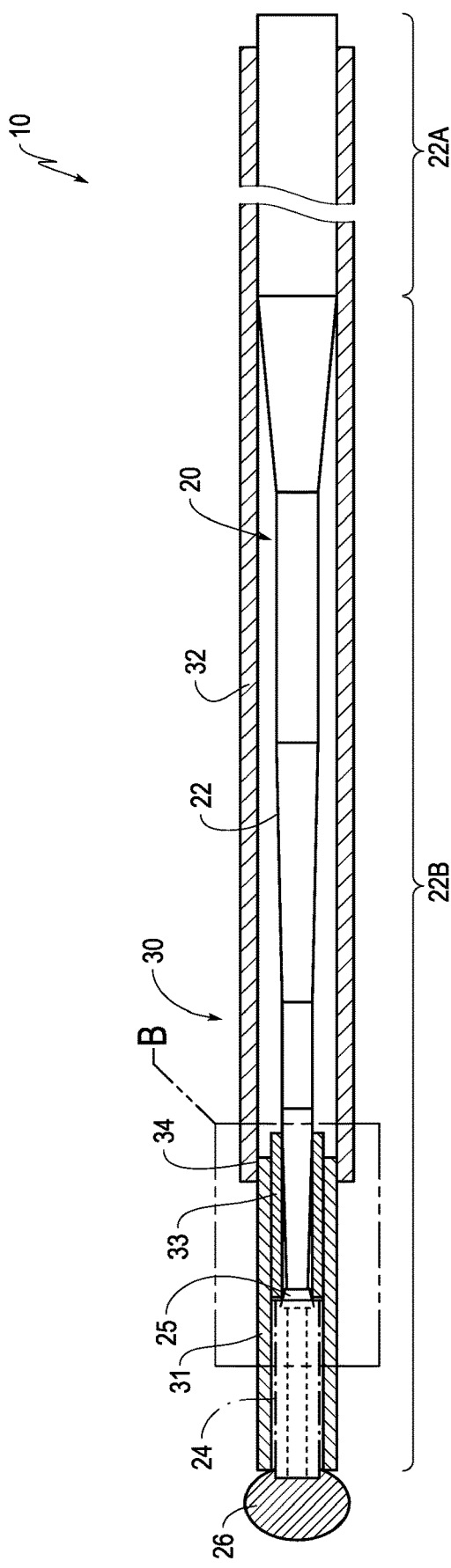
FIG. 2 shows a cross-sectional view taken along line A-A of FIG. 1.
Figure 3:
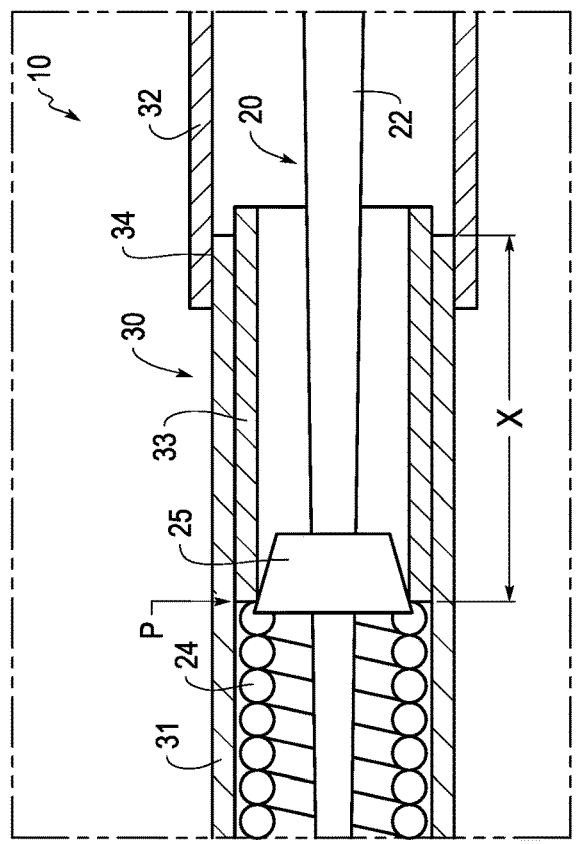
FIG. 3 shows an enlarged view of the portion B of FIG. 2.

Below, embodiments of the present invention will be described with reference to the figures. FIG. 1 shows a front elevational view of a plasma guide wire 10 according to the disclosed embodiments, FIG. 2 shows a cross-sectional view taken along line A-A of FIG. 1, and FIG. 3 shows an enlarged view of the portion B of FIG. 2. Throughout the drawings, the left side corresponds to a distal (front) side to be inserted into a vessel, and the right side corresponds to a proximal (rear) side to be operated by an operator such as a physician.

As shown in FIG. 1, the plasma guide wire 10 includes a guide wire body 20 and an insulating resin tube 30 covering the guide wire body 20. The plasma guide wire 10 has a total length of, for example, 1,800 to 2,000 mm. The plasma guide wire 10 may also be referred to as a high-frequency (RF) guide wire.

As shown in FIG. 2, the guide wire body 20 includes a core shaft 22, a coil 24, a coil-core shaft joining region 25, and a tip 26.

The core shaft 22 is composed of an electrically conductive material, and includes a shaft proximal-end portion 22A and a shaft distal-end portion 22B. The shaft distal-end portion 22B has alternately disposed tubular and tapered portions, and a tubular portion arranged closer to the distal end has a smaller diameter. The core shaft 22 is composed of a material such as, for example, stainless steel (austenite-based stainless steel, martensite-based stainless steel, ferrite-based stainless steel, austenite-ferrite duplex stainless steel, precipitation-hardening stainless steel, and the like), a superelastic alloy (a Ni—Ti alloy and the like), a piano wire, and tungsten.

The coil 24 includes a single element wire spirally wound around on the outer periphery of a region at the distal end side of the core shaft 22. The coil 24 may serve to confer flexibility to the plasma guide wire 10. An electric current from a high frequency generator 40 will flow thorough the core shaft 22 to reach the coil core shaft joining region 25, and then will branch and flow to the distal end of core shaft 22 and to the coil 24. Therefore, the electric current flowing through the coil 24 is smaller than that flowing from the proximal end of the core shaft 22 to the coil-core shaft joining region 25. The total length of the coil 24 is, for example, 40 mm to 50 mm, and the outer diameter of the coil 24 is, for example, 0.24 mm to 0.25 mm, and the diameter of the element wire is, for example, 0.03 to 0.08 mm. The element wire is composed of a material such as, for example, stainless steel (austenite-based stainless steel, martensite-based stainless steel, ferrite-based stainless steel, austenite-ferrite duplex stainless steel, precipitation-hardening stainless steel, and the like), a superelastic alloy (a Ni—Ti alloy and the like), and a radiopacity metal (platinum, gold, tungsten, and the like). It is noted that the coil 24 may be formed by spirally winding a plurality of element wires. Further, the coil 24 may be formed by spirally winding a stranded wire having a plurality of element wires twisted.

The coil-core shaft joining region 25 joins the proximal end of the coil 24 with the core shaft 22, and is composed of a solder material. Solder materials include, for example, aluminum-alloy solder, silver solder, gold solder, zinc, Sn—Pb alloys, Pb—Ag alloys, Sn—Ag alloys, and the like. It is noted that the coil 24 may also be joined to the core shaft 22 through a solder material at the distal end of the coil 24 and/or at the middle portion of the coil 24 in addition to at the proximal end of the coil 24.

The tip 26 is a member having a curved surface and is formed by welding the distal end of the core shaft 22 and the distal end of the coil 24. For welding, arc welding is preferred. Further, arc welding may be of non-consumable electrode types such as TIG welding and plasma welding, or may be of consumable electrode types such as coated arc welding, MAC welding, $CO_2$ gas arc welding, argon-$CO_2$ gas arc welding, MIG welding, and submerged arc welding. Non-consumable electrode types are, however, preferred, and TIG welding is more preferred.

As shown in FIG. 2, the insulating resin tube 30 includes a first insulating resin tube 31, a second insulating resin tube 32, and a third insulating resin tube 33.

The first insulating resin tube 31 is disposed on the outer periphery of the coil 24, and extends proximally from the tip 26 to beyond the coil-core shaft joining region 25. That is, the proximal end of the first insulating resin tube 31 is located proximal to the proximal end of the coil-core shaft joining region 25. The distal end of the first insulating resin tube 31 is joined to the tip 26. The first insulating resin tube 31 is composed of, for example, a fluorine-based resin (e.g., a perfluoroalkoxy alkane (PEA)). The total length of the first insulating resin tube 31 is, for example, 100 mm to 115 mm, and the outer diameter of the first insulating resin tube 31 is, for example, 0.3 mm to 0.35 mm, and the thickness of the first insulating resin tube 31 is, far example, 0.015 mm to 0.02 mm.

The second insulating resin tube 32 is disposed on the outer periphery of the core shaft 22, and extends from the proximal end of the first insulating resin tube 31 to the proximal side of the core shaft 22. The second insulating resin tube 32 is bonded with the first insulating resin tube 31 through a joining region 34. The joining region 34 is formed by bonding the inner surface of the second insulating resin tube 32 at the distal end with the outer surface of the first insulating resin tube 31 at the proximal end via an adhesive. Adhesives include, for example, epoxy resin, acrylic resin, and the like. The second insulating resin tube 32 is composed of, for example, polyimide resin. The total length of the second insulating resin tube 32 is, for example, 1800 mm to 1900 mm, and the outer diameter of the second insulating resin tube 32 is, for example, 0.32 mm to 0.36 mm, and the thickness of the second insulating resin tube 32 is, for example, 0.005 mm to 0.015 mm. The second insulating resin tube 32 is harder than the first insulating resin tube 31. It is noted that the joining region 34 may be bonded with the core shaft 22 via an adhesive.

The third insulating resin tube 33 is arranged inside the first insulating resin tube 31. The distal end of the third insulating resin tube 33 comes into contact with the coil-core shaft joining region 25. As shown in FIG. 3, the third insulating resin tube 33 is disposed so as to cover throughout a region X of the icier periphery of the first insulating resin tube 31, the region X being located proximal to a position P facing the proximal end of the coil 24. That is, the region X extends proximally from the proximal end of the coil 24. The third insulating resin tube 33 further extends proximally beyond the proximal end of the first insulating resin tube 31, and covers, from the inside, the joining region 34 between the first insulating resin tube 31 and the second insulating resin tube 32. The third insulating resin tube 33 can serve to prevent the first insulating resin tube 31 from making contact with the core shaft 22. The third insulating resin tube 33 is composed of, for example, polyimide resin. The total length of the third insulating resin tube 33 is, for example, 60 mm to 80 mm, and the outer diameter of the third insulating resin tube 33 is, for example, 0.23 mm 0.24 mm, and the thickness of the third insulating resin tube 33 is, for example, 0.015 mm to 0.02 mm. The third insulating resin tube 33 is harder than the first insulating resin tube 31. The third insulating resin tube 33 may have a distal end and a proximal end bonded with the core shaft 22 via an adhesive.

Next, an exemplary use of the plasma guide wire 10 is described. The plasma guide wire 10, which can serve as a medical mechanical device for use in percutaneous transluminal coronary angioplasty (PCI), may be used for guiding a device such as a balloon and a stent to an occluded portion of a blood vessel. The distal portion of the plasma guide wire 10 is inserted into a blood vessel, and the proximal portion is operated by an operator such as a physician. Once the distal portion reaches an occluded portion in a blood vessel, an operator pushes, pulls, and/or rotates the plasma guide wire 10 so that the tip 26 may penetrate the occluded portion. However, these operations alone may not be sufficient to penetrate the occluded portion if the occluded portion is hardened due to calcification. If that is the case, a separate plasma guide wire 10 may be introduced into the blood vessel from the opposite side to place the tip 26 of the separate plasma guide wire 10 in the side opposite to the occluded portion. This leads to a state where a pair of the tips 26 are arranged to be opposed to each other across the occluded portion. High-frequency voltage is then applied between the pair of tips 26 to generate plasma between the pair of tips 26, thereby destroying the occluded portion.

Here, a stiffness gap may be created in the plasma guide wire 10 at a portion of the relatively soft first insulating resin tubes 31 where the coil 24 is not present, but the stiffness gap can be reduced by virtue of the presence of the third insulating resin tube 33. This can prevent bending at this portion. Further, the third insulating rosin tube 33 is not disposed on a portion of the relatively soft first insulating resin tubes 31 where the relatively soft first insulating resin tubes 31 covers the coil 24. This can improve the operativity of the distal end side of the plasma guide wire 10, i.e., a portion of the core shaft 22 where the coil 24 is wound around.

In the plasma guide wire 10 as described above, the operativity of the distal end side of the plasma guide wire 10 can be improved (i.e., a portion of the core shafts 22 Where the coil 24 is wound around or/and a portion of the first insulating resin tube where the coil is not present).

Further, a softer resin generally tends to have lower thermal resistance while a harder resin tends to have higher thermal resistance. The first insulating resin tube 31, which is relatively soft and thus has low thermal resistance, may not be able to maintain insulation when making direct contact with the core shaft 22 which is heated to high temperature due to the flow of high-frequency current. However, the third insulating resin tube 33 can serve to prevent the first insulating resin tube 31 from making contact with the core shaft 22. Therefore, insulation of the first insulating resin tube 31 can be better ensured. It is noted that the first insulating resin tube 31 may actually make contact with the coil 24, but the coil 24 is unlikely to be heated to such high temperature. Therefore, insulation will not be compromised. This is because an electric current flowing through the coil 24 upon plasma generation is smaller than that flowing from the proximal end of the core shall 22 through the coil-core shaft joining region 25.

Further, the third insulating resin tube 33, which is harder than the first insulating resin tube 31, can further reduce the stiffness gap created at a portion of the first insulating resin tubes 31 where the coil 24 is not present.

Still further, the third insulating resin tube 33, which is disposed so as to cover, from the inside, the joining region 34 between the first insulating resin tube 31 and the second insulating resin tube 32, can better ensure insulation at the joining region.

Yet further, the third insulating resin tube 33, which comes into contact with the coil-core shaft joining region 25 under a large electric load due to the confluence of an electric current flowing through the coil 24 and an electric current flowing through the core shaft 22, can better ensure insulation at the coil-core shaft joining region 25.

Even further, the third insulating resin tube 33, which is disposed throughout the region X of the inner periphery of the first insulating resin tube 31, the region X being located proximal to the position P facing the proximal end. of the coil 24, can further reduce the stiffness gap created at a portion of the first insulating resin tube 31 where the coil 24 is not present, and can also better ensure insulation of the first insulating resin tube 31.

It is noted that the present invention shall not be limited to the aforementioned embodiments, and the present invention can be implemented according to various aspects as long as they fall within the technical scope of the present invention.

Figure 4:
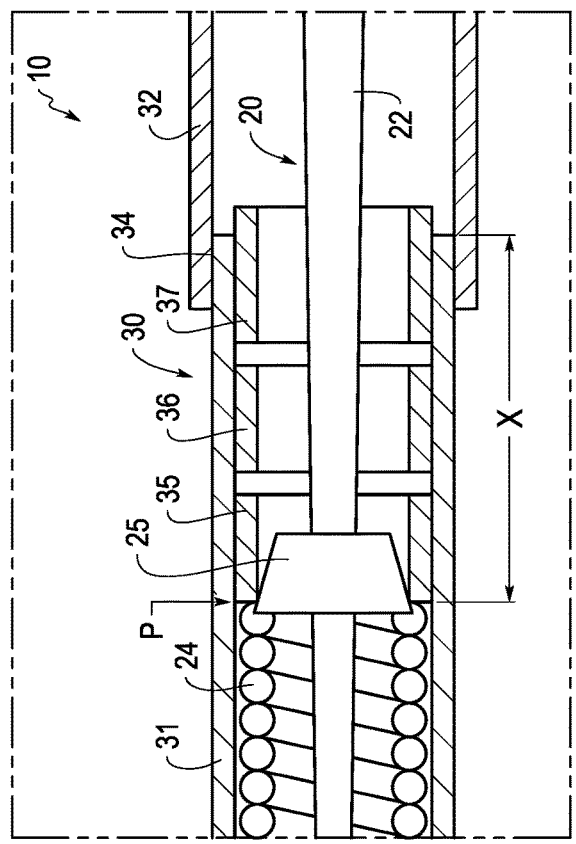
FIG. 4 shows an enlarged view of a plasma guide wire 10 according to the disclosed embodiments.

As shown in FIG. 3, the third insulating resin tube 33 may be disposed throughout the entire region X of the inner periphery of the first insulating resin tube 31, the region X being located proximal to the position P Ewing the proximal end of the coil 24. However, the third insulating resin tube 33 may be disposed at only a portion of the region X. For example, the third insulating resin tube 33 may be divided into three third insulating resin tubes 35, 36, 37 as shown in FIG. 4. It is noted that in FIG. 4, the same reference symbols are given to the same components as already described above. Even in the case of this configuration, the stiffness gap at a portion of the first insulating resin tube 31 where the coil 24 is not present can be reduced by virtue of the presence of the third insulating resin tubes 35, 36, 37. This can prevent bending at this portion. Further, the third insulating resin tubes 35, 36, 37 are not disposed on a portion of the first insulating resin tube 31 where the first insulating resin tube 31 covers the coil 24. This can improve the operativity of the distal end side of the plasma guide wire 10, i.e., a portion of the core shaft 22 where the coil 24 is wound around. It is not noted that the third insulating resin tubes 35, 36, 37 are preferably disposed so as to prevent the first insulating resin tube 31 from making contact with the core shaft 22. Further, any one or two of the third insulating resin tubes 35, 36, 37 may be used. When the third insulating resin tube 35 is used, insulation at the coil-core shaft joining region 25 can be better ensured. When the third insulating resin tube 37 is used, insulation at the joining region 34 can be better ensured.

Plasma may be generated using two of the plasma guide wires 10. For example, the tip 26 of a first plasma guide wire 10 and the tip 26 of a second plasma guide wire 10 can be arranged to be opposed to each other across an occluded portion inside a blood vessel, and then plasma is generated between the pair of the tips 26 while that state is maintained. However, plasma may be generated by another way. For example, plasma may be generated between the tip 26 of the plasma guide wire 10 inserted into a patient's blood vessel and an electrode arranged on the patient's skin. Alternatively, two of the plasma guide wires 10 can be delivered through a blood vessel in a parallel fashion, and plasma may be generated between the tips 26 of them near an occluded portion to destroy the occluded portion.

Figure 5:
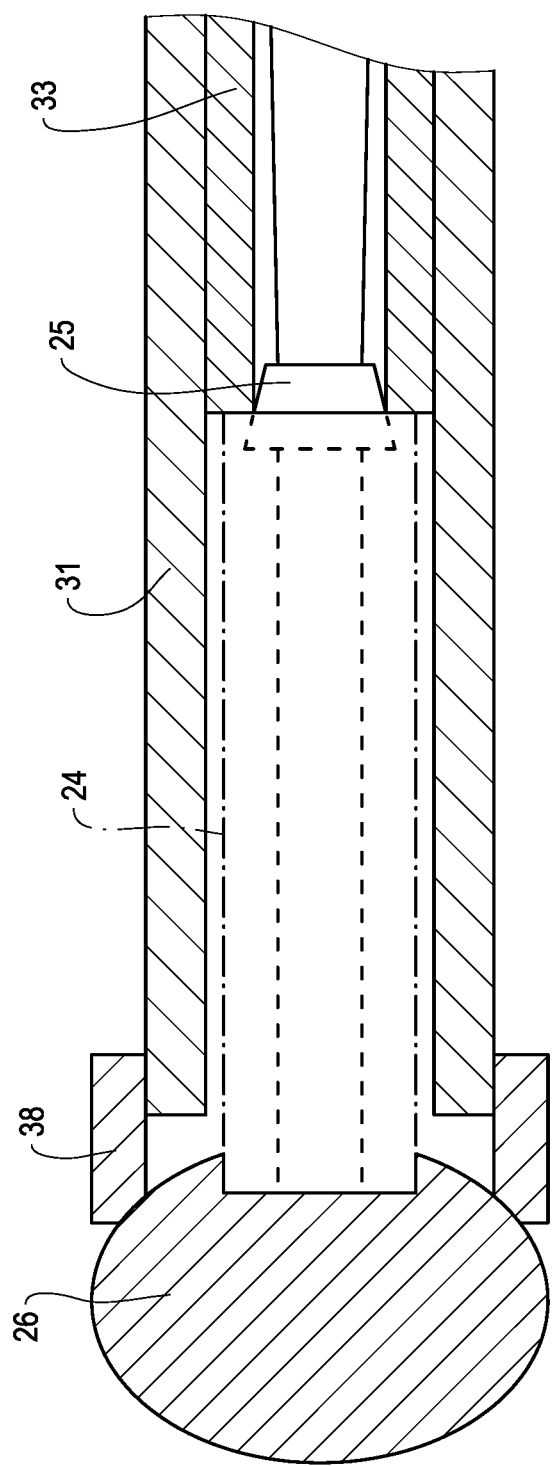
FIG. 5 shows an enlarged view a plasma guide wire 10 according to the disclosed embodiments.
Figure 6:
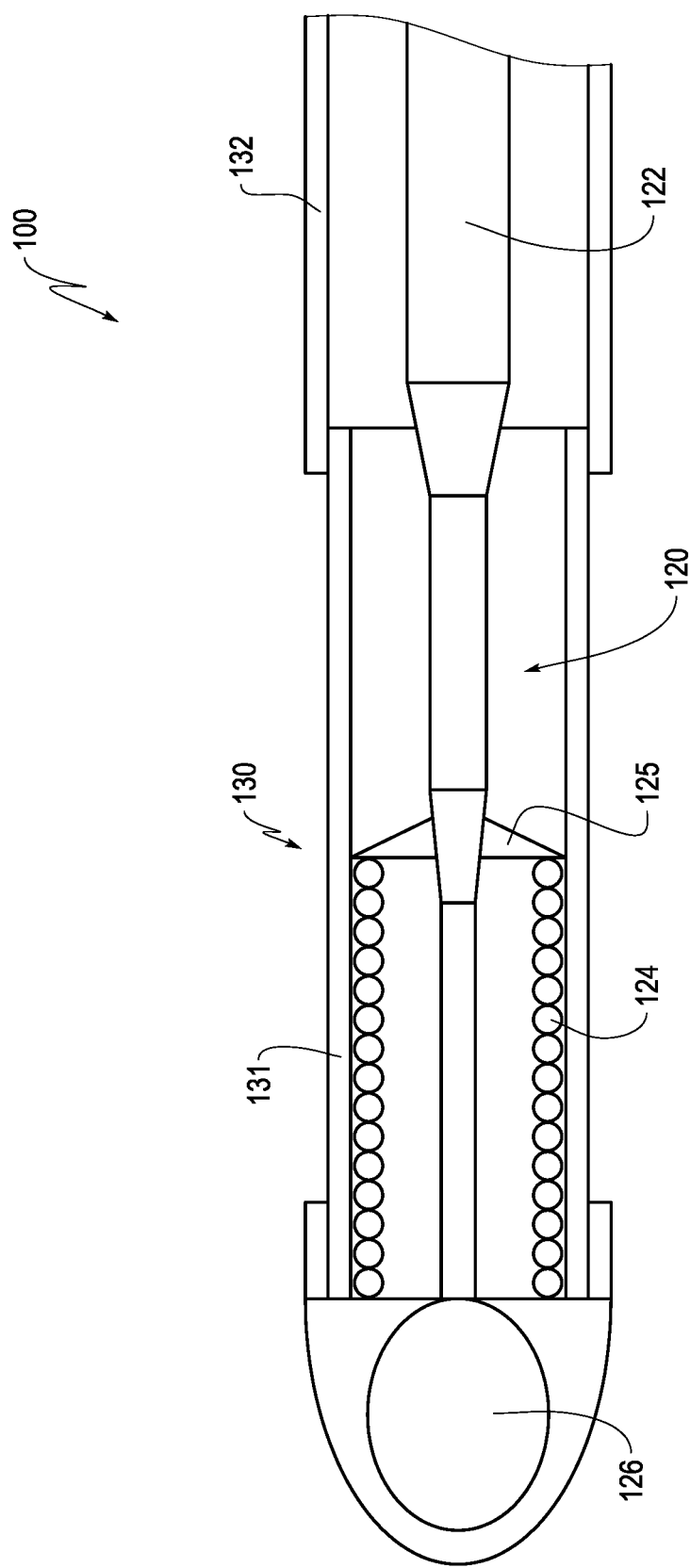
FIG. 6 shows a cross-sectional view of a conventional plasma guide wire 100.

A collar 38 having a ring-like shape and composed of a heat resistant resin (for example, polyimide resin and others) may be disposed at the distal end of the first insulating resin tube 31, and the collar 38 may be joined to the tip 26 as shown in FIG. 5. It is noted that in FIG. 5, the same reference symbols are given to the same components as described above. This configuration can prevent heat damage of the distal end of the first insulating resin tube 31.

The second insulating resin tube 32 may extend to the proximal end face of the shaft proximal-end portion 22A. Alternatively, a proximal portion of the shaft proximal-end portion 22A of the core shaft 22 may extend proximally beyond the proximal end of the second insulating resin tube 32. In this case, the proximal portion of the shaft proximal-end portion 22A is not disposed within the second insulating resin tube 32, and may instead be disposed within another insulating resin tube (a fourth insulating resin tube).

As described above, the third insulating resin tube 33 is harder than the first insulating resin tube 31. However, the configuration shall not be limited to this. For example, the third insulating tube 33 may have the same hardness as the first insulating resin tube 31, or may be softer than the first insulating resin tube 31. Even if these configurations are used, the stiffness gap at a portion of the first insulating resin tubes 31 where the coil 24 is not present can be reduced, leading to improved operativity of the distal end side of the plasma guide wire 10. However, the third insulating resin tube 33 is preferably harder than the first insulating resin tube 31 because the stiffness gap can be further reduced.

As described above, the third insulating resin tube 33 is formed of a material that is harder than that of the first insulating resin tube 31. However, the material shall not be limited to this. For example, the third insulating resin tube 33 may be made of the same material as first insulating resin tube 31, but may be thicker than the first insulating resin tube 31. Even if this configuration is used, the third insulating resin tube 33 can be made harder than the first insulating resin tube 31. It is noted that the hardness for the materials of the first insulating resin tube 31, the second insulating resin tube 32, and the third insulating resin tube 33 means the hardness in terms of Shore hardness or the hardness in terms of durometer hardness. Therefore, the hardness for these materials can be measured using a known testing machine.

It is noted that the plasma guide wire can also be configured, without limitation but for example, as follows.

The third insulating resin tube may be disposed so as to prevent the first insulating resin tube from making contact with the core shaft. In general, a softer resin tends to have lower thermal resistance while a harder resin tends to have higher thermal resistance. The first insulating resin tube, which is relatively soft and thus has low thermal resistance, may not be able to maintain insulation when making direct contact with the core shaft which is heated to high temperature due to the flow of high-frequency current. Here, the third insulating resin tube is disposed so as to prevent the first insulating resin tube from making contact with the core shaft, leading to better ensured insulation of the first insulating resin tube.

The third insulating resin tube may be harder than the first insulating resin tube. This can further reduce the stiffness gap created at a portion of the first insulating resin tube where the coil is not present.

The third insulating resin tube may be disposed so as to cover a joining position between the first insulating resin tube and the second insulating resin tube. This can better ensure insulation at the joining position between the first insulating resin tube and the second insulating resin tube.

The third insulating resin tube may come into contact with the coil-core shaft joining region. This configuration, where the third insulating resin tube comes into contact with the coil-core shaft joining region under a large electric load due to the confluence of an electric current flowing through the coil and an electric current flowing through the core shaft, can better ensure insulation at the coil-core shaft joining region.

The third insulating resin tube may be disposed throughout a region of the inner periphery of the first insulating resin tube, the region being located proximal to a position facing the proximal end of the coil. This can further reduce the stiffness gap created at a portion of the first insulating resin tube where the coil is not present, and can also better ensure insulation of the first insulating resin tube.

The plasma guide wire can he implemented as a medical mechanical device for use in, for example, percutaneous transluminal coronary angioplasty (PCI).

What is claimed is:

1. A plasma guide wire comprising:
a core shaft;
a coil wound around an outer periphery of a region of a distal end side of the core shaft;
a tip joined to a distal end of the core shaft and a distal end of the coil;
a coil-core shaft joining region joining a proximal end of the coil with the core shaft;
a first insulating resin tube disposed on an outer periphery of the coil and extending proximally from the tip to beyond the coil-core shaft joining region;
a second insulating resin tube disposed around an outer periphery of the core shaft, and extending proximally relative to the proximal end of the first insulating resin tube to a proximal side of the core shaft, the second insulating resin tube being harder than the first insulating resin tube;
a third insulating resin tube disposed on at least a portion of a region of an inner periphery of the first insulating resin tube, the region being located proximal to a position facing the proximal end of the coil.

2. The plasma guide wire according to claim 1, wherein the third insulating resin tube is disposed so as to prevent the first insulating resin tube from making contact with the core shaft.

3. The plasma guide wire according to claim 1, wherein the third insulating resin tube is harder than the first insulating resin tube.

4. The plasma guide wire according to claim 1, wherein the third insulating resin tube comes into contact with the coil-core shaft joining region.

5. The plasma guide wire according to claim 1, wherein the third insulating resin tube is disposed throughout the entire region of the inner periphery of the first insulating resin tube that is located proximal to the position facing the proximal end of the coil.

6. The plasma guide wire according to claim 2, wherein the third insulating resin tube is harder than the first insulating resin tube.

7. The plasma guide wire according to claim 2, wherein the third insulating resin tube comes into contact with the coil-core shaft joining region.

8. The plasma guide wire according to claim 2, wherein the third insulating resin tube is disposed throughout the entire region of the inner periphery of the first insulating resin tube that is located proximal to the position facing the proximal end of the coil.

9. The plasma guide wire according to claim 3, wherein the third insulating resin tube comes into contact with the coil-core shaft joining region.

10. The plasma guide wire according to claim 3, wherein the third insulating resin tube is disposed throughout the entire region of the inner periphery of the first insulating resin tube that is located proximal to the position facing the proximal end of the coil.

11. The plasma guide wire according to claim 4, wherein the third insulating resin tube is disposed throughout the entire region of the inner periphery of the first insulating resin tube that is located proximal to the position facing the proximal end of the coil.

12. The plasma guide wire according to claim 1, wherein the third insulating resin tube is disposed on at least a portion of a region of an inner periphery surface of the first insulating resin tube, and the region is located proximally relative to a position facing the proximal end of the coil.

13. The plasma guide wire according to claim 12, wherein the third insulating resin tube is disposed so as to cover at least the portion of the region of the inner periphery surface of the first insulating resin tube.

14. The plasma guide wire according to claim 1, wherein the third insulating resin tube is disposed only within the region located proximal to the position facing the proximal end of the coil.

* * * * *